| United States Patent [19] | [11] | 4,108,869 |
|---|---|---|
| Copelin | [45] | Aug. 22, 1978 |

[54] PREPARATION OF AN ACETAL FROM A DIOL AND ACROLEIN

[75] Inventor: Harry Bugbird Copelin, Wilmington, Del.

[73] Assignee: E. I. Du Pont de Nemours and Company, Wilmington, Del.

[21] Appl. No.: 827,597

[22] Filed: Aug. 25, 1977

[51] Int. Cl.$^2$ .......................................... C07D 319/04
[52] U.S. Cl. .................................................. 260/340.7
[58] Field of Search ...................................... 260/340.7

[56] References Cited

U.S. PATENT DOCUMENTS

| 2,566,559 | 9/1951 | Dolnick et al. ...................... 260/615 |
| 2,729,650 | 1/1956 | Habeshaw et al. ............... 260/340.7 |
| 2,840,615 | 6/1958 | Stautzenberger ................ 260/615 A |
| 2,987,524 | 6/1961 | Fischer et al. ..................... 260/340.7 |
| 3,014,924 | 12/1961 | Brachman ...................... 260/340.7 X |
| 4,024,159 | 5/1977 | Peterson ............................ 260/340.7 |

*Primary Examiner*—Ethel G. Love

[57] ABSTRACT

A process for preparing an acetal from acrolein and a 1,3-diol whereby substantially complete conversion of the acrolein to acetal is attained, by simultaneously reacting and separating by extraction the acetal and water formed from said diol and acrolein reaction, said process comprising continuously feeding a 1,3-diol and an acid catalyst countercurrent to a solvent while continuously feeding acrolein to the solvent and diol, separating the acetal-solvent from the diol-water, optionally separating the acetal and solvent and optionally separating the diol and water.

20 Claims, No Drawings

PREPARATION OF AN ACETAL FROM A DIOL AND ACROLEIN

BACKGROUND OF THE INVENTION

1. Field of Use

This invention relates to a continuous process for preparing a cyclic acetal from a 1,3-diol and acrolein with substantially complete conversion of the acrolein. More specifically, this invention relates to a continuous process for the preparation of a cyclic acetal which comprises reacting acrolein and a 1,3-diol in the presence of a soluble acid catalyst and simultaneously separating by extraction therefrom the product cyclic acetal and water.

2. Prior Art

The reactions of alcohols with aldehydes to form acetals are equilibrium reactions. The degree of conversion to the acetal is limited by the equilibrium constant for the reaction,

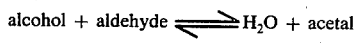

$$K = \frac{C_{H_2O} \cdot C_{acetal}}{C_{alcohol} \cdot C_{aldehyde}}$$

unless one of the products can be removed from the reaction site.

In the above equation, K is the equilibrium constant, and the various C's represent the molar concentrations of reactants and products. The equilibrium constant for the reaction of methanol with acetaldehyde allows only about a 50% conversion to acetal based on the aldehyde, while the reaction of acrolein with 2-methyl-1,3-propanediol (MPD) yields only 65% of acetal based on acrolein under equilibrium conditions.

Several techniques have been used in an attempt to obtain acetals at concentrations higher than the equilibrium concentration. The most common technique used is the completion of the reaction by azeotropic distillation of water with a water-insoluble organic solvent such as benzene or toluene as disclosed in U.S. Pat. No. 2,987,524. Such a process suffers from several basic deficiencies. The high volatility of the acrolein results in excessive quantities coming overhead, which must be separated from the water and returned to the reactor. The overall efficiency is low because low yields of acetal are obtained per volume of reactor space. A high energy consumption, because of the relatively high temperatures required for azeotropic removal of water, is needed. At the temperatures and times required for azeotropic distillation, unsaturated aldehydes, such as acrolein, react to form side products by polymerization and addition of water and alcohols to the carbon-carbon double bond.

Large excesses of one reactant, usually the alcohol, have been used to drive the equilibrium toward higher conversions with more complete utilization of the aldehyde. U.S. Pat. No. 2,566,559 teaches the preferred use of 4 to 5 moles of alcohol per mole of aldehyde. The acetal product must be separated from the large excess of alcohol, and the alcohol recovered and recycled to the process. High molar ratios of aldehyde to alcohol may also be used, but side polymerization reactions and additions to the double bond may consume some of the unsaturated aldehydes.

U.S. Pat. No. 4,024,159 discloses reactions of alcohols or diols with aldehydes that involve formation of liquid acetals wherein greater than equilibrium amounts of acetal are prepared by removal of the organic phase from the aqueous phase.

Thus it is known to react acrolein with a 1,3-diol to produce an essentially equilibrated mixture of reactants and products. However, such processes either involve charging of greater than stoichiometric quantities of reactants to drive the equilibrium reaction to the right or involve the separation of acetal product by distillation or decantation.

There is a need for a process that substantially eliminates the handling of unreacted acrolein from the aforesaid equilibrium reaction while at the same time reduces the energy consumption required for recovery of product by distillation and achieves substantially higher conversions of acrolein to cyclic acetal.

SUMMARY OF THE INVENTION

Now in accordance with the invention, a continuous process has been found for the reaction of an aliphatic 1,3-diol in the presence of a soluble acid catalyst and acrolein and the simultaneous separation of equilibrium products therefrom by solvent extraction that allows the equilibrium reaction to continue until substantially complete conversion of the acrolein is reached.

Thus, the present invention is directed to an improvement in the continuous process for reacting acrolein with a polyol in the presence of an acid catalyst to form a cyclic acetal and water, wherein the improvement comprises reacting the acrolein with an aliphatic 1,3-diol of 3 to 10 carbon atoms in the presence of a soluble acid catalyst and simultaneously therewith separating by solvent extraction the cyclic acetal and water produced by continuously contacting a solvent with said reactants, to extract the cyclic acetal, as it is formed, with the solvent while retaining the water, as it is formed, with the 1,3-diol said solvent being a nonpolar hydrocarbon or chlorohydrocarbon solvent which is immiscible with the 1,3-diol and which boils at 10° to 300° C. The solvent flow is countercurrent to the flow of diol. Further, separations of the cyclic acetal-solvent and diol-water for the purpose of recovering acetal and recycling solvent, water and diol can be accomplished.

The process of this invention results in substantially complete conversion of the acrolein to cyclic acetal. What is meant by substantially complete conversion of the acrolein to cyclic acetal is a single pass conversion of at least 98% by weight of the acrolein to acetal. By single pass is meant the conversion of acrolein to acetal without any recycling of recovered reactants.

Accordingly, in a preferred embodiment of this invention, a cyclic acetal is prepared from acrolein and a 1,3-diol whereby substantially complete conversion of the acrolein to acetal is attained, said process comprising (1) continuously feeding a 1,3-diol containing an acid catalyst near the top portion of a vertical reactor extractor column, a solvent near the bottom portion of the column, acrolein into the middle portion of the column, (2) optionally separating the water from a flow from the bottom of the column comprising diol-acid-water by distillation, optionally recycling the thus separated diol and acid to the 1,3-diol feed to the reactor extractor, optionally washing with water the flow from the top of the column comprising solvent and acetal to remove traces of unreacted diol, separating the solvent and acetal from the wash water and optionally distilling said solvent and acetal from the diol extractor column to separate the solvent from the acetal, optionally recycling the solvent to the bottom portion of the reactor extractor and recovering the acetal. The scope of the process of this invention also includes the aforesaid process wherein the 1,3-diol containing acid catalyst is fed into the bottom portion of the column, a solvent into the top portion of the column and acrolein into the middle of the column where the solvent density is great enough to permit a reversal of the flow.

A solvent is required in the process of the present invention to enhance the separation of the water-diol phase from the acrolein-acetal phase. The amount of solvent may vary widely. Generally at least an amount of solvent equivalent to the acrolein feed is desirable. The weight ratio of solvent to acrolein generally varies from 0.2:1 to 10:1. Ratios greater than 10:1 can be used, but there is not sufficient incentive to use such amounts of solvent. Ratios lower than 0.2:1 will not give adequate extraction of the acetal to achieve the substantially complete conversions of this invention.

The solvent of the present invention may be any solvent which is unreactive under the process conditions of this invention, which is sufficiently nonpolar to form a separate phase in contact with the diol employed and which boils at $-10°$ to $300°$ C. Olefins may hydrolyze and are therefore too reactive to be within the scope of the solvent of this invention. The solvents of the present invention may be aromatic or saturated aliphatic hydrocarbons, chlorohydrocarbons or mixtures thereof. Representative examples of the solvents of this invention include benzene, toluene, hexane, heptane, cyclohexane, methyl cyclohexane, tetrahydronaphthalene, dicahydronaphthalene, methyl naphthalene, pentane, butane, isobutane, ethyl benzene, xylene, trimethyl benzene, tetra and penta methyl benzenes, chlorobenzene, chlorotoluene, chloroxylenes and mixed saturated hydrocarbon fractions. The preferred solvents are aromatic hydrocarbons and saturated aliphatic hydrocarbons boiling in the range of $-10°$ to $120°$ C. Thus the preferred solvents are selected from the group consisting of benzene, toluene, hexane and heptane and lower boiling simple saturated aliphatics such as pentanes and butanes. The most preferred solvents are those aromatic hydrocarbons and saturated aliphatic hydrocarbons that boil in the range of $0°$ to $80°$ C. Of said aromatic hydrocarbons and saturated aliphatic hydrocarbons that boil in the range of $0°$ to $80°$ C, the most preferred are benzene, hexane and heptane. The solvents selected from the group consisting of benzene, hexane and heptane are the most desirable.

The amount of the 1,3-diol added to the process of this invention may vary widely. Generally an amount in excess of the stoichiometric equivalent quantity of the 1,3-diol that is reacted with acrolein is required. Generally these amounts are expressed as a mole ratio range from 1.5:1 to 10:1 of diol:acrolein.

The 1,3-diols of this invention are any aliphatic 1,3-diols of 3 to 10 carbon atoms, preferably 3 to 6 carbon atoms. Representative examples of the 1,3-diol of this invention include 1,3-butanediol; 1,3-propanediol; 2,2-dimethyl-1,3-propanediol; 2-methyl-2,4-pentanediol; 2-methyl-1,3-propanediol; 2,4-pentanediol; 2-ethyl-1,3-propanediol; 1,3-pentanediol; 2,4-hexanediol; 1,3-hexanediol; 2,2-diethyl-1,3-propanediol; 1,3-heptanediol; 1,2-diethyl-3-propyl-1,3-propanediol; 1,3-decanediol; 1,3-nonanediol; etc. The 1,3-diols of this invention may be defined by the general formula

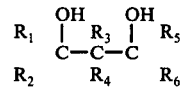

where $R_1$, $R_2$, $R_3$, $R_4$, $R_5$ and $R_6$ are H or alkyl groups of 1 to 4 carbon atoms, preferably 1 to 2 carbon atoms and the total carbon atoms in the general formula are from 3 to 10, preferably 3 to 6. The preferred alkyl group is methyl. The preferred 1,3-diols of this invention are 1,3-butanediol; 1,3-propanediol; 2-methyl-1,3-propanediol; 2,2-dimethyl-1,3-propanediol and 2-methyl-2,4-pentanediol; and the most preferred are 1,3-butanediol and 2-methyl-1,3-propanediol.

The acrolein-diol reactions of the process of this invention are acid-catalyzed with conventional soluble acid catalysts. Soluble mineral acids, such as hydrochloric acid, sulfuric acid and phosphoric acid catalyze the reaction strongly. Organic sulfonic acids, such as p-toluenesulfonic acid, are also excellent catalysts.

The process of the present invention is preferably conducted in a reaction vessel that permits the solvent extracted acetal to flow upward while the diol extracted water flows downward. However, the process of this invention includes the use of solvents of greater density whereby the solvent extracted acetal flows downward while the diol extracted water flows upward. The reaction vessel thus provides means for mixing the reactants and then allows the two immiscible liquids (solvent-acetal and diol-water) to separate. The extractive liquids, the solvent and the diol, are passed countercurrent to each other in the reaction vessel. Thus, the reaction vessel can be any vessel that permits such a separation such as a tower of various proportions depending on the flow desired, or a vertical vessel wherein the height is sufficient to permit sufficient time for separation of the two liquid phases.

The process can also be conducted continuously in a series of reaction vessel(s) with decanters for liquid separations or with a separation zone in the reaction vessel(s). For example, in a series of three conventional reactor vessels equipped with a stirrer the diol feed can be fed to the first vessel, the acrolein fed to the second vessel and the solvent fed to the third vessel with the discharge from each vessel separated in a decanter so that the acetal-solvent separated can be pumped to the preceding vessel while the glycol-water flows forward. Likewise a column equipped with alternative stirred and packed settling zones can be used.

The process of this invention is preferably operated in a single reactor extractor column with a separating zone before and after each reaction zone. In a preferred embodiment of this invention, a Schaible extractor is used. The concept of extractor column operation is most conveniently used to separate the products of the reaction by a process of liquid extraction in which the acetal is removed in a solvent from the one end of the column and the water and acid catalyst are removed in excess diol from the other end of the column. By this means, essentially complete acrolein conversion can be attained due to the major separations which occur within the column. In an example, hexane is fed to the bottom portion of a reaction extractor column, diol containing a small amount of sulfuric acid is fed near the top of the column, and acrolein is fed near the middle. As the solvent rises, it extracts product acetal from the diol phase. The acrolein is extracted from the solvent to the diol phase where it reacts to acetal and water. Toward the top of the tower, the water content decreases, thus improving acrolein conversion. As the diol phase flows down the column, it becomes richer in water thereby forcing extraction of acetal product by the solvent. The diol-and-water stream from the bottom of the column can be vacuum flashed to remove most of the water and the diol with some acid catalyst can be recycled to the top of the column with the diol feed. The solvent acetal from the top of the column can be washed with water in another column or an extension of the reactor extractor to remove small amounts of acid and diol present. If the streams from the reactor extractor are to be purified, distillation columns can also be used. The solvent-acetal can be distilled to remove a major proportion of the solvent, thereby also removing small amounts of water from the product cyclic acetal.

The cyclic acetal product of this invention is useful in the preparation of 1,4-butanediol which can be used to prepare tetrahydrofuran, which is useful as a solvent.

The operating parameters of the process are highly interrelated. To obtain optimum results, the temperature, contact time, column efficiency, and acid concentration must be counterbalanced to give, on one hand, high acrolein conversion, and, on the other, low by-product formation. High acrolein conversion is favored by high temperatures, high acid concentration and long contact time. Low byproducts are favored by low temperatures, low acid and short contact time. Thus, the temperature is usually in the range of from 0° to 100° C with a preferred range being from 10° to 60° C. The best temperature in each case will be determined by the reactants used. At temperatures lower than 10° C the reaction may be too slow to be commercial. At temperatures above 60° C, unsaturated aldehydes such as acrolein tend to undergo side reactions. The acid concentration in the feed diol generally is from 0.01 to 10%, with a preferred range being 0.1 to 1.0%. The rate of acetal production will range from 100 to 2,000 or more lb/day/cu ft of reactor volume, with a preferred range of 400 to 800 lb/day/cu ft. These rates will be attained by balancing temperatures, rates of various feed streams, and acid concentrations. Of great importance is to maximize efficiency of the reactor extractor column employed as this permits higher acrolein conversions and rates while minimizing by-products. The reaction rate is limited by the heat removal ability of the extractor vessel. Heat removed can be controlled by the use of a heat exchanger either internal or external to the vessel. Increasing the solvent and diol feed rates may also be used to remove heat. Additionally, the feeding of supercooled solvent may be used to remove heat.

Most advantageously the reactor extractor vessel comprises a Schaible extractor column which permits maximization of fluid contact in the column. A Schaible extractor employs alternate agitated and packed settling sections in the extractor thereby giving high contact efficiency. The settling sections are packed with any packing material that would not interfere with the reaction that is taking place such as stainless steel pall rings, glass helices and various types of ceramic rings and saddles.

In the separation of the flows from the reactor extractor that involve two phases, any apparatus known to be useful for such separations may be used, for example, the aqueous phase may be separated from the solvent-acetal phase by a decanter. However, separation may be accomplished in the extractor itself by providing more settling space for the flows before leaving the extractor.

The invention is further illustrated but is not intended to be limited by the following examples in which all parts and percentages are by weight unless otherwise specified.

EXAMPLE 1

The reactor extractor column employed in this example consisted essentially of a 1.5 inch × 5 feet glass tube set vertically and fitted with connections to allow introduction of feeds and withdrawal of products. The 1.5 inch O.D. glass tube had a solvent feed point 1 inch from the bottom, a acrolein feed point 22 inches above the solvent feed, a diol acid feed point into the top of the tube 4 inches below the solvent-acetal exit point and 2 inches above the packing in the tube, a solvent-acetal exit 6 inches above the packing and a diol-water-acid exit at the bottom. The tube was packed to a height of about 49 inches with 3/16 inch glass helices to improve contacting. Small stainless steel bellows pumps were used to feed the acrolein, solvent and diol. Diol-acid and diol-water-acid mixtures were handled in gum rubber tubing. Copper and Teflon ® were used for acrolein, solvent and product acetal containing streams.

Feed rates were set as follows:

| | |
|---|---|
| Acrolein | 200 g/h |
| Solvent (hexane) | 200 g/h |
| 1,3-diol (1,3-butanediol containing 0.5% $H_2SO_4$) | 430 g/h |

The 1,3-butanediol-water phase was withdrawn from the bottom of the column at a rate of 155 g/hr and the product acetal-hexane phase from the top at a rate of 675 g/hr. Analyses by gas chromatograph of samples from the top and bottom of the reactor extractor showed a 98% conversion to acetal based on the acrolein with negligible amounts of product acetal in the glycol-water effluent. The temperature slowly rose in that section of the column above the acrolein feed point until it reached about 55° C where it leveled out. The rate of acetal produced was 470 g/hr/liter of reactor volume (700 lb/day/cu ft).

COMPARATIVE EXAMPLE A

A mixture of 1 molar equivalent of 2-methyl-1,3-propanediol (MPD) and a 1.1 molar equivalent of acrolein was passed through a column (¼ inch × 6 inches) of 10 ml of strongly acidic cationic exchange resin (Dowex MSC-1) at the rate of 0.55 g/min. The bed was cooled with circulating water at 25° C and the maximum temperature in the resin bed was 35° C. The reaction product (30.7 g) divided into 2 layers — an acetal layer (26.6 g) and an aqueous layer (4.1 g). Analysis showed that 75% of the acrolein was converted to 2-vinyl-5-methyl-1,3-dioxane.

COMPARATIVE EXAMPLE B

The addition of 0.05 ml of 37% hydrochloric acid to a mixture of 18.02 g (0.20 moles) of 2-methyl-1,3-propanediol and 12.12 g (0.216 moles) acrolein at 30° C produced a rapid temperature rise to 48° C. The temperature was reduced to 30° C and maintained at that temperature for 2 hours with cooling. The reaction mixture divided into 2 layers — 25.62 g of acetal layer and 4.84 g of aqueous layer. The conversion of acrolein to acetal was 82%.

COMPARATIVE EXAMPLE C

The reaction of 26 g (0.25 mole) of 2,2-dimethyl-1,3-propanediol and 15.4 g (0.275 mole) of acrolein was catalyzed with 0.1 ml of 37% hydrochloric acid. At a controlled reaction temperature of 35° to 40° C, separation into 2 layers began within 2 minutes. The conversion of acrolein to acetal was 84%. A similar reaction at 27° C produced 2 layers in 40 minutes and gave the same conversion to acetal.

COMPARATIVE EXAMPLE D

A mixture of 1.0 molar equivalent of 1,3-butanediol and 1.0 molar equivalent of acrolein was stirred over 10 ml of Dowex 50W cationic exchange resin at 20° C. Samples of the reaction mixture were analyzed until the maximum conversion had been achieved in 2 hours. The reaction mixture consisted of 2 layers. The conversion to 2-vinyl-4-methyl-1,3-dioxane was 91%.

COMPARATIVE EXAMPLE E

A mixture of 1.0 molar equivalent of 1,3-butanediol and 1.0 molar equivalent of acrolein was stirred in the presence of 0.15% hydrogen chloride at 20° C. After 3 hours of reaction, 90% of the 1,3-BAD and of the acrolein were converted to 2-vinyl-4-methyl-1,3-dioxane.

COMPARATIVE EXAMPLE F

A mixture of 1.0 molar equivalent of 2-methyl-1,3-propanediol and 1.0 molar equivalent of acrolein was passed through a column of 50 ml of Amberlyst 15 cationic exchange resin at a temperature of 25° to 30° C. Eighty-nine percent of the reactants had been converted to 2-vinyl-5-methyl-1,3-dioxane.

While the invention has been described in considerable detail in the foregoing, it is to be understood that such detail is solely for the purpose of illustration and that variations can be made by those skilled in the art without departing from the spirit and scope of the invention except as set forth in the claims.

What is claimed is:

1. In a continuous process for reacting acrolein with a polyol in the presence of an acid catalyst to form a cyclic acetal and water, the improvement comprising reacting an aliphatic 1,3-diol of 3 to 10 carbon atoms at a temperature of from 0° to 100° C with acrolein at a mole ratio of diol:acrolein of from 1.5:1 to 10:1 in the presence of a soluble acid catalyst and simultaneously therewith, separating by solvent extraction the cyclic acetal and water formed by contacting countercurrently a solvent with said reactants at a weight ratio of 0.2:1 to 10:1 of solvent:acrolein to extract the cyclic acetal as it is formed with the solvent while extracting water as it is formed with the 1,3-diol, said solvent being a nonpolar hydrocarbon or chlorohydrocarbon solvent which is immiscible with the 1,3-diol and which boils at −10° to 300° C.

2. The improvement of claim 1 wherein the aliphatic 1,3-diol has 3 to 6 carbon atoms.

3. The improvement of claim 1 wherein the aliphatic 1,3-diol is 1,3-butanediol.

4. The improvement of claim 1 wherein the aliphatic 1,3-diol is 2-methyl-1,3-propanediol.

5. The improvement of claim 1 wherein the solvent is selected from the group consisting of benzene, hexane and heptane.

6. The improvement of claim 1 wherein the reaction and the simultaneous solvent extraction is conducted in a reactor extractor column.

7. The improvement of claim 1 wherein the boiling point of the solvent is from 0° to 80° C.

8. The improvement of claim 6 wherein the 1,3-diol containing soluble acid catalyst is fed into the extractor column near the top portion thereof, the solvent is fed into the column near the bottom portion thereof and the acrolein is fed into the column at the middle portion and a solvent and cyclic acetal mixture is taken out of the top of the column and a 1,3-diol and water mixture is taken out of the bottom of the column.

9. The improvement of claim 8 wherein the solvent and acetal mixture is washed with water to remove unreacted 1,3-diol and then distilled to separate the acetal from the solvent.

10. The improvement of claim 8 wherein the aliphatic 1,3-diol has 3 to 6 carbon atoms.

11. The improvement of claim 8 wherein the aliphatic 1,3-diol is 1,3-butanediol.

12. The improvement of claim 8 wherein the aliphatic 1,3-diol is 2-methyl-1,3-propanediol.

13. The improvement of claim 8 wherein the solvent is selected from the group consisting of benzene, hexane and heptane.

14. The improvement of claim 8 wherein the boiling point of the solvent is from 0° to 80° C.

15. The improvement of claim 9 wherein the solvent separated from the acetal is recycled back to the feed into the bottom portion of the column and the 1,3-diol is separated from the water and recycled to the 1,3-diol feed into the column.

16. The improvement of claim 15 wherein the solvent boiling point is from 0° to 80° C.

17. The improvement of claim 15 wherein the aliphatic 1,3-diol is 1,3-butanediol.

18. The improvement of claim 15 wherein the aliphatic 1,3-diol is 2-methyl-1,3-propanediol.

19. The improvement of claim 15 wherein the solvent is selected from the group consisting of benzene, hexane and heptane.

20. The improvement of claim 14 wherein the aliphatic 1,3-diol has 3 to 6 carbon atoms.

* * * * *